Figure 1:
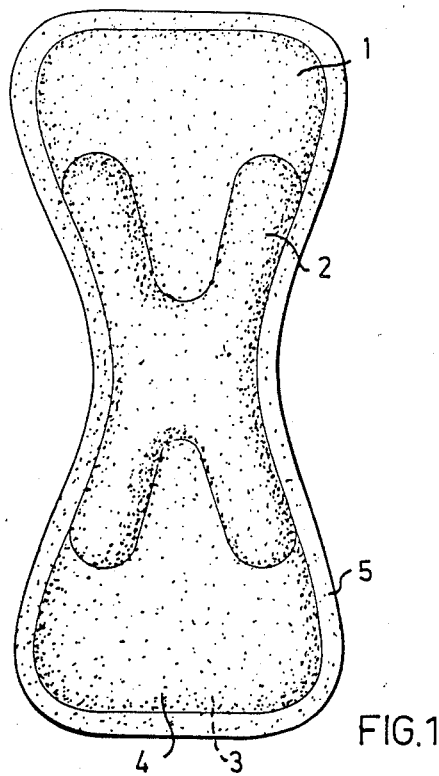

United States Patent [19]

Hermansson

[11] Patent Number: 4,828,555

[45] Date of Patent: May 9, 1989

[54] ABSORBENT ARTICLE SUCH AS A DIAPER OR INCONTINENCE PROTECTOR

[75] Inventor: Jonas Hermansson, Göteborg, Sweden

[73] Assignee: Molnlycke AB, Goteborg, Sweden

[21] Appl. No.: 53,831

[22] PCT Filed: Sep. 24, 1986

[86] PCT No.: PCT/SE86/00426

§ 371 Date: May 18, 1987

§ 102(e) Date: May 18, 1987

[87] PCT Pub. No.: WO87/01914

PCT Pub. Date: Apr. 9, 1987

[30] Foreign Application Priority Data

Oct. 3, 1985 [SE] Sweden ............................. 8504584

[51] Int. Cl.[4] .................. A61F 13/16; A41B 13/02
[52] U.S. Cl. ................. 606/379; 604/385.1; 604/358
[58] Field of Search ............... 604/358, 378, 379, 376, 604/385

[56] References Cited

U.S. PATENT DOCUMENTS

| 3,364,931 | 1/1968 | Hirsch. | |
| 3,528,422 | 9/1970 | Hodaj | 604/385 R |
| 4,184,498 | 1/1980 | Franco | 604/379 |
| 4,624,666 | 12/1986 | DeRossett et al. | 604/378 |

FOREIGN PATENT DOCUMENTS

| 3136014 | 4/1983 | Fed. Rep. of Germany. |
| 3333245 | 7/1984 | Fed. Rep. of Germany. |
| 427985 | 5/1983 | Sweden. |
| 1259865 | 1/1972 | United Kingdom. |
| 2139096 | 11/1984 | United Kingdom. |

Primary Examiner—Stephen C. Pellegrino
Attorney, Agent, or Firm—Young & Thompson

[57] ABSTRACT

An elongated absorbent article, such as a diaper or an incontinence protector, comprises an absorption body disposed in a casing and having between its two ends a crotch portion. The absorption body comprises a bottom sheet (1) and a top sheet (2), the top sheet being adapted to lie in contact with the wearer and to serve as a spacer means between the skin of the wearer and the bottom sheet. The top sheet (2) has parts (9, 10) which are located along two side-edge portions of the bottom sheet and which define laterally between them at least one space (7) around a wetting point of the article. These parts (9, 10) located along the side-edge portions of the bottom sheet have an extent such that the article has within the regions of the parts (9, 10) a much higher flexural resistance than the remainder of the article, such that when the article is positioned on the wearer, the portion of the article located between those parts (9, 10) is curved both laterally and transversely such as to impart a basin-like configuration to the space around the wetting point (7).

11 Claims, 1 Drawing Sheet

U.S. Patent     May 9, 1989     4,828,555

ABSORBENT ARTICLE SUCH AS A DIAPER OR INCONTINENCE PROTECTOR

The present invention relates primarily to an absorbent article such as a diaper or an incontinence protector.

One demand on such a product is that it must be capable of absorbing discharged body fluid without leaking.

In certain types of urinary incontinence, emptying of the urinary bladder takes place in a sudden, uncontrollable manner so that a large quantity of body fluid is discharged within a short period of time. For an adult, this quantity may amount to as much as 15–30 cl of fluid flowing out at a time. An example of this type of urinary incontinence is the so-called pressure incontinence. Elderly women are those most frequently suffering from pressure incontinence, the symptoms being an urgent, uncontrollable feeling of pressure appearing quite unexpectedly and most often leading to the bladder being emptied before the sufferer has had the time to reach a lavatory.

The absorbency of conventional diapers is not sufficient for rapidly taking up the large quantities of fluid common in pressure incontinence, and extreme leakages of urine resulting in wetted clothes are therefore a rule rather than an exception for individuals suffering from this type of incontinence.

Great efforts have been made to accomplish diaper constructions for the purpose of solving this problem, which have so far proved unsuccessful, however.

One suggestion to a solution can be found, for example, in the European Patent Specification No. 124 365.

An absorbent body designed in accordance with the above publication is said to be capable of absorbing and retaining during a short period of time a large quantity of discharged body fluid. Said absorbent body, which is intended for diapers, sanitary napkins and incontinence protectors, is substantially rectangular and has two receptacles for body fluids, accomplished by means of compression, said receptacles being in communication with a duct which is also formed by compression.

Discharged body fluid is passed via the communication duct to the receptacles to be absorbed there by the absorbent body. However, due to the comparatively narrow dimension of the duct and the relatively limited receptacle areas, a diaper having such an absorbent body has to be positioned absolutely correctly in the user's crotch to fulfill its function and to actually collect discharged body fluid. When moving, the user will otherwise be exposed to the imminent risk of the diaper slipping somewhat out of alignment, so that body fluid comes outside the duct and flows over the edge of the diaper thereby wetting the user's clothes.

According to said patent specification, the rectangular shape of this prior art absorbent body is justified by a desire to widen the communication duct between the receptacles in that the diaper when used is compressed in the crotch region so as to assume a "boat shape" in order presumably to reduce diaper leakage.

In fact, however, the known, soft and flexible diaper will instead crumple up into a clumsy package between the user's legs blocking in this way the communication duct so that no body fluid can be led off. As a result, the efficiency of this diaper will be just as good or bad as other conventional diapers without any duct system being compressed thereinto, since body fluid will start to flow out and onto the user's clothes as soon as the absorbent material disposed in the crotch region of the diaper has been saturated. Moreover, a diaper of the soft, flexible type described above will easily give rise to the formation of cross-folds as the user moves, these fols then leading fluid sideways out of the diaper.

There have been made other attempts as well to overcome the problem of taking up large amounts of fluid for instance in cases of pressure incontinence. As an example, there is previously known a method of incorporating a liquid-distributing layer in the absorbent body for transporting fluid away from the wetting point, making in this manner the greatest possible part of the absorbent body accessible for absorption. The efficiency of this type of liquid-transport is however insufficient for the large quantities of fluid frequently occurring and therefore, the problem of leakage still remains to a large extent.

A similar liquid-distributing effect is obtained to a certain degree if the absorbent body is compressed along lines extending in its longitudinal direction.

There is further previously known a method of building up the absorbent body of two layers; one upper, porous layer primarily absorbing discharged body fluid, and one lower, more compact layer gradually sucking up fluid from the upper layer. In this manner there is gained a certain, but often insufficient receptacle effect in the upper layer.

A still further conventional method of attempting to reduce leakage is characterized by a plastic film being folded around the absorbent body so as to cover its underside, the edge margins and a portion extending along each longitudinal edge of the absorbent body upper side. In this way, however, the liquid-permeable portion of the upper side of the absorbent body will be diminished thereby increasing the risk of leakage, especially if the diaper is slantingly displaced.

Also, attempts have been made to produce a fluid-receiving duct by the application of elastic means across the area of the absorbent body intended to face the crotch region of the user. Such a duct may certainly have a positive effect but has unfortunately proved insufficient for those suffering from heavy incontinence involving the large amounts of fluid occurring in such cases.

As appears from the aforesaid, a great deal of effort has been expended in attempts to solve the above-described problem of developing absorbent products in the form of diapers and incontinence protectors being capable of, without leaking and within a very short period of time, collecting and absorbing large volumes of liquid. Despite all these efforts, no satisfactory solution to the problem has been attained so far, since the resulting products have either given rise to more leakage than desirable, or they have led to a compromise between the need for security against leakage and the need for comfort and discretion which must always be satisfied by articles such as diapers and incontinence protectors.

With the present invention however, the problem in question has now been overcome. Primarily, this achievement is the result of the absorbent body being built up of a bottom layer cõhsisting of at least one stratum and a top layer composed of one stratum or several mutually spaced strata, said top layer being intended for placement next to the user's skin while simultaneously serving as a spacer means between the user's skin and the bottom layer, and being designed to at least laterally define a basin-like space around the so-called wetting point. Because the article is thicker and thus more rigid in the areas around the basin-like space as compared to its smaller volume in the area below it, said space will be maintained and expanded when the article is applied to the body of the user.

There are disclosed in the following a number of different embodiments of the invention.

With the absorbent body consisting of two layers of absorbent material in combination with the specific design of the upper one of said layers which is intended to face the user's skin, there is achieved the advantage that a diaper in accordance with the invention will be forced during use to assume a predetermined configuration. When in use, this diaper will namely transform to a shape presenting a duct extending along its longitudinal centerline as well as a basin-like zone located at least at one end of said duct. Both the basin-like zone and the centrally extending duct will be surrounded by portions of the diaper upper layer as a result of this layer forming ridges alongside the edges of the absorbent body. These ridges, which constitute the diaper portions intended to face the user's skin, act like tight basin walls sealing around the so-called wetting point while also serving as spacer means for the absorbing bottom layer in the absorbent body. Thereby, only the smallest possible portion of the wet diaper will touch the user's skin, avoiding in this manner any discomfort and skin irritation caused by moisture. With the absorbent body built up in this manner, a diaper in accordance with the invention will thus assume an optimal configuration with regard to capability of collecting and retaining large and unexpectedly discharged amounts of fluid. Discharged fluid is collected and initially retained in the basin-like zone and the longitudinally extending duct of the diaper, and is then absorbed by the material in the absorbent body.

This utilization of the absorbent body in order to make absorbent articles such as diapers or incontinence protectors capable of forcibly conforming during use to a specific shape promoting their intended purpose, is an inventive concept imparting to the resulting articles properties making them superior to hitherto known articles of similar types. By the excellent liquid-absorbing and leakage-preventing properties incorporated in the absorbent body itself, this article will be most useful in cases of adult urinary incontinence.

An important demand on diapers for adults suffering from urinary incontinence is discrete use. Such diapers must also provide sufficient security for the user to feel safe without having to worry about leakage occurring upon a sudden, unexpected discharge from the bladder. To meet the need for security against leakage, the diapers used up to now have been made large in size and clumsy as they would otherwise be incapable of momentarily sucking up sufficient amounts of discharged body fluid. These voluminous and awkward diapers, difficult to hide in ordinary clothing, could be experienced by the user as mentally disturbing, inhibiting a normal social life involving work and personal relations.

An absorbent article according to the invention could however, in relation to the amounts of fluid it is momentarily capable of handling in normal cases, be made both small in size and discrete in shape without jeopardizing security against leakage.

An article in accordance with the invention could to advantage also be used for infant incontinence. Today's conventional diapers are most frequently a combination of an absorbent body and a plastic backing, many times in the form of integrally made, so-called all-in-one diapers. To reduce the risk of leakage in diapers of this type, they have to be applied to the baby in tightly sealing contact around the legs. This tight seal is generally secured by the use of elastic means disposed in the crotch region along the edges of the backing portion of the diaper unit. Such elastic means often make the diaper unpleasant to wear due to chafing resulting in skin irritation. The plastic material will further seal tightly to the sensitive skin in the crotch region, which may add to the irritation.

A further disadvantage associated with conventional diapers is the increased costs caused by the use of elastic means, which costs are particularly unfortunate with regard to disposable articles.

With a diaper in accordance with the invention, however, the need for tightly sealing elastic means will be eliminated since the sealing function is already initially incorporated in the diaper construction in that the raised portions of the absorbent body facing the baby's skin constitute buffering ridges protecting against leakage. There is thus no need for any chafing and cost-increasing elastic means in such a novel diaper.

Another advantage is that the favorable configuration of the novel diaper will remain intact even though the diaper may slip somewhat out of alignment due to the baby's movements, whether this displacement occurs in the forward, backward or sideward direction. Conventional, flat diapers, on the other hand, are liable to fold together causing thereby discharged urine to flow out to the side thereof. This is, inter alia, the reason why these diapers require specific sealing means around the thighs of the infant.

Figure 2:
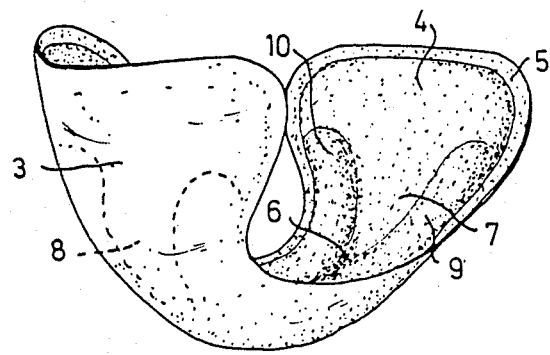

The invention will be described in more detail below with reference to an exemplary embodiment shown in the accompanying drawing, wherein FIG. 1 is a plan view of a diaper made according to the invention, illustrating the side thereof intended to face the user's skin; whereas FIG. 2 is a perspective view of said diaper in its state of use as seen obliquely from one side.

The diaper shown in FIGS. 1 and 2 comprises an absorbent body built up of a lower, flat layer 1 and a superimposed, substantially X-shaped upper layer 2. This absorbent body is accommodated in a casing consisting of a lower, liquid-impermeable surface layer 3 and an upper, liquid-permeable surface layer 4 intended to face the user's skin, said two layers being interconnected around the absorbent body beyond its edge 5. When applied for use to the human body, the diaper will assume the configuration shown in FIG. 2. The X-shaped upper layer 2 of the absorbent body will then act as a shape-controlling means enforcing the formation of two basin-like zones 7, 8 and an interconnecting duct 6 extending therebetween. In the embodiment shown, the diaper is made symmetrical with regard to a transverse centerline. When applying the diaper to the user's body, the so-called wetting point, i.e. the spot on the diaper first reached by the user's urine, will be located right in the center of the basin situated at the front of the user. The duct 6 and the two basin-like zones 7, 8 are defined along the diaper long sides by ridges 9, 10 serving to prevent leakage and to keep the more soaked duct and basin portions 6 and 7, 8 spaced away from the user's skin.

Discharged body fluid is collected in the duct 6 and the basin-like zones 7, 8 to be subsequently sucked into the absorbent material. Because fluid is allowed to pass between the basins 7, 8 via the duct 6, also the basin 8 located at the back of the user can be utilized for the absorption of fluid. In this manner the entire absorbent mass of the diaper will be accessible for absorption. In prior art diapers however, only a small area around the wetting point is available, whereas large portions of the absorbent body remain unutilized.

The diaper shown in FIGS. 1 and 2 may be used either in combination with elastic baby pants, or together with ordinary, not too wide underpants keeping the ridges 9, 10 of the diaper in close contact with the user's body.

The two layers 1, 2 of the absorbent body may to advantage be composed of so-called cellulose fluff pulp and may then preferably be formed by airlaying and compression of the pulp in molds provided to serve this purpose. The layers can then be individually manufactured for subsequent interconnection. The liquid-permeable casing material 4 facing the skin of the wearer during use is suitably connected both to the upper layer 2 of the absorbent body and to freely exposed portions of the liquid-permeable casing material 3 at the underside of the diaper.

If the bottom layer in the absorbent body is given a higher degree of compression than the top layer, a liquid-expelling effect from the top to the bottom layer can be attained by the density gradient in a manner known per se.

Alternatively, the two layers of the absorbent body can be made of different material. For example, a non-absorbent synthetic fiber wadding can be used for the top layer.

Additional embodiments of articles performed in accordance with the invention are conceivable within the scope of the appended claims.

For example, a diaper may be provided at its liquid-impermeable backside with binder beads or a foam-plastic coating for preventing the diaper from being displaced during use in relation to the underpants situated closest thereto.

Another example is the possibility of providing the inventive diaper with resilient means in the form of elastic ribbons or the like, as it would be possible to achieve an increased basin-producing effect by the application of such means along the short sides of the diaper, whereas similar means applied across the crotch region thereof would intensify the duct shape desired in this area.

Naturally, the bottom layer of the absorbent body need not be uniformly thick but may, in order to enhance the stability and absorbency of the article, be made somewhat thicker in the crotch region, said thickness then to advantage gradually decreasing towards the ends.

An article according to the invention need of course not be hourglass-shaped but may have any other suitable configuration such as T-shape, for example.

The inventive article may also be provided with folding lines in order to facilitate its shaping during use. Such folding lines are suitably applied along the longitudinal center duct and along the ridges defining the basin-like zones in order for the article to fold more easily during use to achieve the formation of said longitudinal center duct and said basin-like zones.

I claim:

1. An elongated absorbent article, such as a diaper or an incontinence protector, comprising an absorption body disposed in a casing and having between its two ends a crotch portion, the absorption body comprising a bottom layer (1) and a top layer (2), said top layer having a thickness such that said top layer is adapted to serve as a spacer means between the wearer and the bottom layer; said top layer (2) having parts (9, 10) which are located along two sideedge portions of the bottom layer and which define laterally between them at least one space (7) around a wetting point of the article; the thickness of said parts being such that the article has within the regions of said parts (9, 10) a much higher flexural resistance than the remainder of said article, such that when the article is positioned on the wearer the portion of the article located between said parts (9, 10) is curved both laterally and transversely in a basin-like configuration around said wetting point (7).

2. An absorbent article according to claim 1, in which the top layer (2) extends across the whole width of the crotch part of the diaper, such that the crotch part is highly resistance to flexural forces and resistant to deformation forces; said parts (9, 10) comprising branches which diverge outwardly from the crotch part at least in a direction toward an end of the article and which serve as borders defining the basin-like space (7).

3. An article according to claim 1, in which the article is symmetrical about a transverse centerline of the crotch part of said article.

4. An article according to claim 1, in which both the top layer (2) and the bottom layer (1) of the article are connected with the casing (3, 4) embracing the absorbent body on the sides thereof which face the wearer's body in use.

5. An article according to claim 1, in which the bottom layer (1) is compressed more compactly than the top layer (2).

6. An article according to claim 5, in which the top and bottom layers (2, 1) consist of two mutually separate pieces which have been subsequently joined together.

7. An article according to claim 1, in which the two layers (1, 2) included in the absorbent body are made from mutually different materials.

8. An article according to claim 7, in which the top layer (2) is made of synthetic fiber wadding and the bottom layer (1) of cellulose fluff.

9. An article according to claim 1, in which the absorbent body is formed of airlaid and compressed cellulose fluff.

10. An elongated absorbent article, such as a diaper or an incontinence protector, comprising an absorption body disposed in a casing and having between its two ends a crotch portion, the absorption body comprising a bottom layer (1) and a top layer (2), said top layer having a thickness such that said top layer is adapted to serve as a spacer between the wearer and the bottom layer; said top layer (2) being X-shaped and having a longitudinal midportion coinciding with said crotch portion of said absorbent article.

11. An elongated absorbent article, such as a diaper or an incontinence protector, comprising an absorption body disposed in a casing and having between its two ends a crotch portion, the absorption body comprising a bottom layer (1) and a top layer (2), said top layer having a thickness such that said top layer is adapted to serve as a spacer means between the wearer and the bottom layer; said top layer (2) comprising a V-shaped portion composed of two parts (9, 10) which diverge toward an end of the absorbent article and converge toward said crotch portion to define laterally between them at least one space (7) around a wetting point of the article.

* * * * *